US006156952A

United States Patent [19]
Bryant et al.

[11] Patent Number: 6,156,952
[45] Date of Patent: Dec. 5, 2000

[54] HIV TRANSGENIC ANIMALS AND USES THEREFOR

[75] Inventors: Joseph L. Bryant, Rockville; William C. Reid, Frederick; Harry G. Davis, Jr., Woodbine, all of Md.

[73] Assignee: Constituent Institution of the University of Maryland System, Baltimore, Md.

[21] Appl. No.: 09/058,113

[22] Filed: Apr. 9, 1998

[51] Int. Cl.$^7$ .......................... A01K 67/00; A01K 67/03; C12N 15/00; G01N 33/00

[52] U.S. Cl. .................................. 800/11; 800/9; 800/14; 800/21; 800/3

[58] Field of Search .................................. 800/8, 3, 2, 21, 800/25, 11, 14; 435/320.1, 325, 375; 424/9.1

[56] References Cited

U.S. PATENT DOCUMENTS

| | | | |
|---|---|---|---|
| 5,489,742 | 2/1996 | Hammer et al. | 800/2 |
| 5,574,206 | 11/1996 | Jolicoeur | 800/2 |

FOREIGN PATENT DOCUMENTS

| | | |
|---|---|---|
| 0 528 360A2 | 8/1992 | European Pat. Off. . |
| WO 91/04327 | 4/1991 | WIPO . |
| WO 92/20790 | 5/1992 | WIPO . |
| WO 94/00568 | 1/1994 | WIPO . |
| WO 97/49373 | 12/1997 | WIPO . |

OTHER PUBLICATIONS

Clements JE et al. Clinical Microbiol. Rev. 9:100–117, 1996.
Dickie P et al Virology 185:109–119, 1991.
Tinkle BT et al J. Clin. Invest. 100:32–39, 1997.
Naldini L. et al. "Efficient Transfer, integration, and Sustained Long–term Expression of the Transgene in Adult Rat Brains Injected With a Lentiviral Vector", *Proc. Natl. Acad. Sci. USA*, vol. 93, No. 21, Oct. 15, 1996, pp. 11382–11388, XP002114690.
Finco O. et al. "Induction of CD4+ T Cell Depletion in Mice Doubly Transgenic for HIV gp120 and Human CD4" *Eur. J. Immunol.* vol. 27, No. 6, Jun. 1997, pp. 1319–1324, XP002114691.
Klotman P. and Notkins, A. "Transgenic Models of Human Immunodeficiency Virus Type–1" *Curr. Top Microbiol. Immunol.* vol. 206, pp. 197–122, XP002114694.

International Search Report for PCT/US98/07821 dated Sep. 22, 1999.
Berthold, E., et al., "cis–Acting Elements in Human Immunodeficiency Virus Type 1 RNAs Direct Viral Transcript to Distinct Intranuclear Locations," *Journal of Virology*, pp. 4667–4682, Jul. 1996, vol. 70.
Connor, R., et al., "Characterization of the Functional Properties of env Genes from Long–Term Survivors of Human Immunodeficiency Virus Type 1 Infection," *Journal of Virology*, pp. 5306–5311, Aug., 1996, vol. 70.
De, S., et al., "Human Chorionic Gonadotropin Hormone Prevents Wasting Syndrome and Death in HIV–1, Transgenic Mice," *The Journal of Clinical Investigation*, vol. 99, No. 7, pp. 1484–1491, Apr. 1997.
Dickie, Peter, "HIV Type 1 Nef Perturbs Eye Lens Development in Transgenic Mice," *Aids Research and Human Retroviruses*, vol. 12, No. 3, 1996, 177–189.
Dickie, Peter, "Models of HIV Type 1 Proviral Gene Expression in Wild–Type HIV and MLV/HIV Transgenic Mice," *Aids Research and Human Retroviruses*, vol. 12, No. 12, 1996, 1103–1116.
Hopp, Thomas, "Human Chorionic Gonadrotropin Hoodwinks Gallo," *Nature Biotechnology 15:834*, Oct. 1997.
Leonard, J., et al., "Development of Disease and Virus Recovery in Transgenic Mice Containing HIV Proviral DNA," Science vol. 242, pp. 1665–1670, Dec. 23, 1988.
Ray, P. et al., "bFGF and its Low Affinity Receptors in the Pathogenesis of HIV–Associated Nephropathy in Transgenic Mice," *Klaney International*, vol. 40, pp. 759–772, 1994.
Santoro, T., et al., "Growth Failure and Aids–like Cachexia Syndrome in HIV–1 Transgenic Mice," *Virology*, 201:147–151, 1993.
Whitmer, K., et al., "HIV–1 Expression During Early Mammalian Development," *AIDS*, vol. 6, No. 10, 1133–1138, 1992.

*Primary Examiner*—Jasemine Chambers
*Assistant Examiner*—Ram Shukla
*Attorney, Agent, or Firm*—Foley, Haog & Eliot, LLP; Isabelle M. Claus; Beth E. Arnold, Esq.

[57] ABSTRACT

The invention provides transgenic animals comprising a lentiviral transgene, such as an HIV transgene. Also within the scope of the invention are cells and eggs from the transgenic animal. Further included are methods for identifying therapeutic compounds for preventing lentiviral infection and treating associated disease (e.g. AIDS).

13 Claims, 2 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

TAGTAGCATG CTCTCTCGAC GCAGGACTCG GCTTGC      36

(2) INFORMATION FOR SEQ ID NO:2:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:2:

ACCTCCTGCA GCACAGGTAC CCCCATAATA GACTGTG      37

(2) INFORMATION FOR SEQ ID NO:3:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:3:

```
ATGATCTGCA GTTCTATTCC TTCGGGCCTG TCG                                33
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

```
AGCAGCAGGA AGCACTATGG                                               20
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

```
CCAGACTGTG AGTTGCAACA G                                             21
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

```
GAGCCAGTAG ATCCTAGACT AGAGC                                         25
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

```
CTTAGGCATC TCCTATGGCA GGAA                                          24
```

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

-continued (xi) SEQUENCE DESCRIPTION: SEQ ID NO:8:

ACCTCGCATG CGAAGAAGCG GAGACAGCGA CGAAG                35

(2) INFORMATION FOR SEQ ID NO:9:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:9:

TGACGCTGAC GGTACAGGCC                                20

HIV TRANSGENIC ANIMALS AND USES THEREFOR

Statement of Rights

This invention was made with government support under DE09170 awarded by the National Health Institutes. The government has certain rights in the invention.

BACKGROUND OF THE INVENTION

Human immunodeficiency virus (HIV) is an etiological agent of Acquired Immune Deficiency Syndrome (AIDS). AIDS was first reported in the United States of America in 1981. As of January 1997, approximately 1.5 million cases of AIDS in adults and children had been reported to the World Health Organization (WHO); however, because reporting is difficult, WHO estimates that there were more than 8.4 million cases, about 580,000 of which reside in the United States. However, the number of HIV infected individuals is much higher: as of January 1997, WHO estimated that there were approximately 29.4 million HIV infected individuals world-wide, with about 1 million in the United States. It has been estimated that by the year 2000, between 40 and 100 million individuals will be infected with HIV.

HIV, which has also been referred to as lymphadenopathy-associated virus (LAV), HTLV-III, or AIDS related virus (ARV), is a lentivirus from the family of retroviruses and is composed of RNA consisting of about 9,700 base pairs, three gag proteins (having molecular weights of 55,000, 24,000 and 17,000 daltons), a reverse transcriptase (molecular weights of 66,000 and 51,000 daltons have been detected), three glycoproteins (two molecules having molecular weights of 120,000 and 41,000 daltons, and their precursor, a molecule with a molecular weight of 160,000 daltons, hereinafter abbreviated as gp120, gp41 and gp160, respectively) which comprise the envelope, and other components. Exposed, envelope proteins are particularly important for viral infection and therefor also, the prevention thereof. As a result of proteolysis, gp1 60 is cleaved into gp120 and gp41. Gp41 is a transmembrane protein which is incorporated into the lipid bilayer of the viral envelope, while gp120 is exposed on the outside of the envelope and some of it is released from the virus. Both gp41 and gp120 possess many sugar-binding sites, and about half of the gp120 molecule is comprised of sugars. The gp120 molecule binds to the CD4 antigens on the surface of cells, in particular helper T cells. Once HIV is bound to CD4 via gp 120, another env gene product, gp41, mediates fusion between the membranes of the cell and the virus allowing the core of the virus to enter the cell. Gp120, which is expressed on the plasma membrane of infected cells before virus is released, can bind to CD4 on another cell, initiating a membrane fusion event resulting in syncytia formation, and HIV genomes can be passed between the fused cells directly.

The env gene (gp120) is the primary determinant of cell tropism for both HIV and Simian Immunodeficiency Virus (SIV). Variable region 3 (V3) of gp120 is a key component within env that determines cell tropism. The efficiency of replication and the ability to induce the syncytia formation are also affected by changes in the V3 loop.

The first HIV virus isolated is referred to as HIV-1 and is generally described in several articles, e.g., Barre-Sinoussi et al., Science 220:868, 1983; Gallo et al., Science 224:500, 1984; Popovic et al., Science 224:497, 1984; and Levy et al., Science 225:840, 1984, each of which is hereby incorporated by reference. Various isolates of HIV-1 have been obtained from North America, Western Europe and Central Africa. These isolates differ somewhat in their nucleotide sequence, but the proteins they encode are generally antigenically cross-reactive.

A second virus related to HIV-1 has been isolated and termed HIV-2 (Guyader et al., Nature 326:662, 1987; Brun-Vezinet et al., The Lancet 1:128, 1987; and Clavel et al., Science 233:343, 1986). The genetic organization of HIV-2 is similar to that of HIV-1. Of the two distinct subtypes, HIV-1 is predominant and found throughout the world, whereas HIV-2 has been isolated primarily in West African countries such as Guinea Bissay, Ivory Coast, and Senegal, whith some cases also identified in the Americas and western Europe. Epidemiological studies suggest that the incubation period for HIV-2 for the development of disease is longer than for HIV-1.

HIV isolates from around the world were found to differ in nucleotide sequence. These sequences have been collected in a specialized database (Myers et al. (1994) Los Alamos National Laboratory, Los Alamos, N.Mex.). Two major groups of HIV has been identified. Viruses of group M (for "main") are responsible for the majority of infections worldwide; group O (for "outgroup") is a relatively rare group currently found in Cameroon, Gabon, and France. Group M can be divided into at least eight distinct subtypes or clades (A through H) (Myers, supra; Louwagie et al. (1995) J. Virol. 69:263). Isolates from HIV-1 from different clades may differ by 30–40% in the amino acid sequence of the gp120 SU protein; isolates within a lade vary from 5% to 20%. Clade B predominates in North America and Europe and lade E predominates in northern Thailand. Similarly, there are five HIV-2 sequence subtypes.

A group of viruses isolated from monkeys, termed simian immunodeficiency virus (SIV or STLV-III), is related to HIV-1 and HIV-2, particularly the latter. See Daniel et al., Science 228:1201–1204 (1985); Kanki et al., Science 230:951–954 (1985); Chakrabarti et al., Nature 328:543–547 (1987); and Ohta et al., Int'l. J. Cancer 41:115–222 (1988). Members of this viral group exhibit minor variations in their genomic sequences, and have some differences in their restriction enzyme maps.

Although human CD4 is essential for HIV infection, it is not sufficient. Expression of human CD4 on rodent cells renders them capable of binding virus but still nonpermissive for fusion or infection (Maddon et al. (1986) Cell 47:333). The host component or coreceptors, sometimes referred to as the "fusion receptors", were identified only recently. These coreceptors are receptors for chemokines (i.e. small proteins which serve as chemoattractants in inflammation) and they permit HIV infection of virtually any mammalian or avian cell that expresses human CD4 (Bates (1996) Cell 86:1–3). The most important coreceptors are CXCR4 (also called "fusin" or "LESTR") (Endres et al. (1996) Cell 87:745; Feng et al. (1996) Science 272:872) and CCR5 (Akhatib et al. (1996) Science 272:1955; Choe et al. (1996) Cell 85:1135; Deng et al. (1996) Nature 381:661; Doranz et al. (1996) Cell 85:1149; and Dragic et al. (1996) Nature 381:667). CXCR4 is the receptor for the chemokine SDF-1, whereas CCR5 serves as a receptor for the chemokines MIP-1α and β and RANTES. These coreceptors play a crucial function for viral entry into cells, and they are also the principal determinants of tropism among CD4+ cells.

Two distinct types of HIV-1 have been identified based on the cells in which they replicate in vitro. Viruses that replicate in T cell lines, but not macrophages or monocytes, are referred to as T tropic, whereas viruses with the complementary specificity are referred to as M tropic. The tropism is at least a function of the coreceptor: M tropic viruses can use only CCR5 for entry, and T tropic viruses use CXCR4. A few dual tropic isolates capable of using both are also known. T tropic viruses often cause infected cells to fuse with uninfected cells if the latter express both human CD4 and CXCR4. Such viruses are referred to as 'syncytium-inducing" (SI). All isolates can infect activated T cells freshly isolated from peripheral blood, which are present in PBMC cultures, since such cells express both CXCR4 and CCR5. Furthermore, cell tropisms are not fixed and can change when the virus is passaged in cell culture (Metlzer et al. (1990) Immunology Today 11:217; Levy (1993) Microbiol. Rev. 57:183).

Two animal species (i.e., man and chimpanzee) are known to be susceptible to HIV infection, but only in man does the disease develop. HIV-1 transgenic mice carrying intact copies of the HIV-1 provirus have been obtained (Leonard et al. (1988) Science 242:1665). These mice develop a spontaneous and fatal disease that mimics some of the features described in human AIDS. Other HIV-1 transgenic mice carrying the HIV-1 proviral DNA in which deletions have been introduced have also been produced (see, e.g., Dickie et al. (1991) Virology 185:109; Santoro et al. (1994) Virol. 201:147).

However, none of these transgenic mice closely model the development of AIDS in humans. In particular, none of the HIV transgenic mice express gp120 on the surface of their T cells. Thus, syncytium formation between HIV infected cells and CD4+ cells, e.g., T cells, which is reported to occur in humans and which is in fact the mechanism by which HIV is transmitted from one cell to another without the production of infectious HIV particles, does not occur in HIV transgenic mice. In addition, since HIV transgenic mice do not express gp120 on the surface of infected cells and all of the neutralizing antibodies in humans have mapped to the envelope protein, gp160, or one of its component parts (gp120 or gp41), transgenic, HIV mice are not particularly useful for developing human HIV vaccines.

Thus, there is a need for animal models of AIDS and other lentiviral diseases, which more closely model infection and disease progression as it occurs in humans.

SUMMARY OF THE INVENTION

In one aspect, the present invention features non-human animal models of lentiviral (e.g., HIV) infection and development of disease (e.g. AIDS). Preferred non-human animals comprised of a lentiviral transgene are larger than a mouse. Other preferred non-human, transgenic animals are smaller than a monkey. A particularly preferred non-human, transgenic animal is a transgenic rat.

In preferred embodiments, the transgene comprises essentially all of a viral genome, i.e., the transgene comprises at least about 70%, at least about 80%, at least about 90% or at least about 95% of a wild-type viral genome. Also within the scope of the invention are transgenic animals in which the transgene comprises a smaller portion of the wildtype virus, (e.g. less than about 70% of the viral genome). For example, the transgenic animal can comprise a transgene encoding a single protein.

In a preferred embodiment, the transgenic, non-human animal is comprised of an HIV transgene. Exemplary HIV proteins for inclusion in the transgene include an envelope protein (e.g., gp120 and gp40), a reverse transcriptase, a protease, an integrase, a ribonuclease, a nucleocapsid core factor (gag), a transcriptional activator (e.g., tat and vpr) or proteins encoded by the genes vif, vpu, and nef In another preferred embodiment, the transgenic, non-human animal expresses the HIV proteins. In a particularly preferred embodiment, the animal expresses the HIV protein gp120 on the surface of its peripheral blood mononuclear cells (PBMCs). In a further preferred embodiment, the transgenic, non-human animal expresses at least one HIV coreceptor (e.g. CCR5 or CXCR4).

In another embodiment, in addition to the lentiviral transgene, the transgenic, non-human animal is comprised of at least one additional transgene. In a preferred embodiment, the additional transgene is a human CD4 receptor gene. Expression by the animal of both HIV and human CD4 allows the HIV particles produced to enter the CD4 expressing cells, thus resulting in HIV infection. In another preferred embodiment, the additional transgene is an HIV coreceptor, such as CCR5 or CXCR4, which further aids in HIV infection. In a further preferred embodiment, the additional transgene is a gene involved in a disease or condition that is associated with AIDS (e.g. hypertension, Kaposi's sarcoma, cachexia, etc.).

In another preferred embodiment, the non-human animal containing an HIV transgene exhibits at least one symptom or phenotype characteristic of human HIV infection and/or development of AIDS (e.g. development of cataracts, cachexia or lesions (e.g. skin lesions, for example, resulting from psoratic dermatitis, hyperkerstotic lesions, kidney sclerotic lesions or inflammatory lesions of the central nervous system).

In another aspect, the invention features methods for producing the transgenic animals described herein. A preferred method comprises the steps of: (a) obtaining a non-human animal egg containing a lentivirus transgene; (b) implanting the egg of step (a) into a female non-human animal; (c) selecting offspring containing the transgene to thereby obtain a founder animal; and (d) crossing the founder animal with another animal preferably of the same species, but opposite sex, to thereby produce a transgenic animal comprising a lentivirus transgene.

In one embodiment, the lentiviral transgene, in step (a), is an HIV transgene. In a preferred embodiment, the HIV transgene is infectious. For example, the transgene can be supplied by a wild-type HIV provirus, e.g, an HIV-1 or HIV-2 provirus or strain thereof Alternatively, the transgene can be a modified form of a wild-type provirus, such as a provirus having a deletion, substitution or addition of at least one nucleotide to the viral genome. For example, a provirus can be modified by replacing the transcriptional control element in an LTR of the HIV provirus with another transcriptional control element, for example to alter the tropism of the virus. A provirus can also be modified by deleting a portion of, or mutating, at least one HIV gene, to thereby inactivate at least one HIV protein, e.g, gag, pol, env, or tat. In another embodiment, the HIV transgene is non-infectious. For example, an HIV provirus can be rendered non-infectious by deleting a portion of gag and pol or by mutating at least one LTR of the provirus.

In a further aspect, the invention features non-human animal cells containing a lentivirus transgene, e.g., an HIV transgene. For example, the animal cell (e.g. somatic cell or germ cell (i.e. egg or sperm)) can be obtained from a lentivirus transgenic animal. Transgenic somatic cells or cell lines can be used, for example, in drug screening assays. Transgenic germ cells, on the other hand, can be used in generating transgenic progeny, as described above.

In yet further aspects, the invention features methods for using the non-human transgenic animals, cells and cell lines of the invention for investigating molecular and cellular mechanisms of lentiviral mediated pathogenesis (e.g. the molecular and cellular mechanisms of the skin lesions, CNS disturbances, heart and kidney disease, which is associated with human HIV infection); as well as for identifying compounds and vaccines for treating and/or preventing lentivirus (e.g. HIV) infection and disease (e.g. AIDS) development.

A preferred in vitro assay for identifying molecular antagonists which, for example, interfere with a lentivirus ligand-receptor interaction, as well as molecular agonist which, for example, function by activating a lentivirus protein (e.g. receptor) is comprised of the steps of: (a) incubating transgenic cells expressing a protein (e.g. receptor) known to be involved in lentivirus infection with a test compound; and (b) detecting the interaction between the lentivirus protein and the test compound, wherein the presence of an interaction indicates that the test compound may be an inhibitor of lentivirus infection. In another embodiment, in step (a), the test compound is incubated with the transgenic cell in the presence of a compound, which is a binding partner (e.g. a receptor ligand) to the expressed protein and the interaction between the test compound and the lentivirus protein or between the lentivirus binding partner and the lentivirus protein is detected.

In other embodiments, cell based assays can be used to identify compounds which modulate expression of a lentivirus gene, modulate translation of a lentivirus mRNA, or which modulate the stability of a lentivirus mRNA or protein. A preferred assay comprises the steps of: (a) incubating a transgenic cell, which expresses a particular lentivirus protein with a test compound; and (b) comparing the amount of the lentivirus protein produced to that produced by the same cell which has not been contacted with the test compound.

In a further embodiment, the effect of a test compound on transcription of a particular lentivirus gene can be determined by a transfection assay, which uses a reporter gene operatively linked to at least a portion of the promoter of a lentivirus gene.

A preferred in vivo assay for identifying a compound which is useful for treating or preventing a disease or condition associated with lentivirus infection is comprised of the steps of. a) administering a test compound to a lentivirus transgenic animal; and (b) observing at least one phenotype associated with infection by the lentivirus, wherein a change in phenotype indicates that the test compound is capable of treating or preventing the disease or condition. In a preferred embodiment for identifying an effective vaccine, the transgenic non-human animal is made with an infectious lentivirus transgene, the compound is a lentivirus antigen or combination of antigens and the phenotype is an immune response. In a particularly preferred embodiment for identifying effective HIV vaccines, the transgenic non-human animal is made with an infectious HIV transgene, alone or in conjunction with a transgene encoding a CD4 receptor (e.g. a human CD4 receptor) and/or an HIV co-receptor transgene (e.g. CCR or CXCR4).

In a further aspect, the invention features methods for treating subjects infected with a lentivirus or preventing infection by a lentivirus, comprising administering to the subject an effective amount of a compound identified according to an assay of the invention.

Other aspects of the invention are described below or will be apparent to those skilled in the art in light of the present disclosure.

DETAILED DESCRIPTION OF THE INVENTION

General

Figure 1:
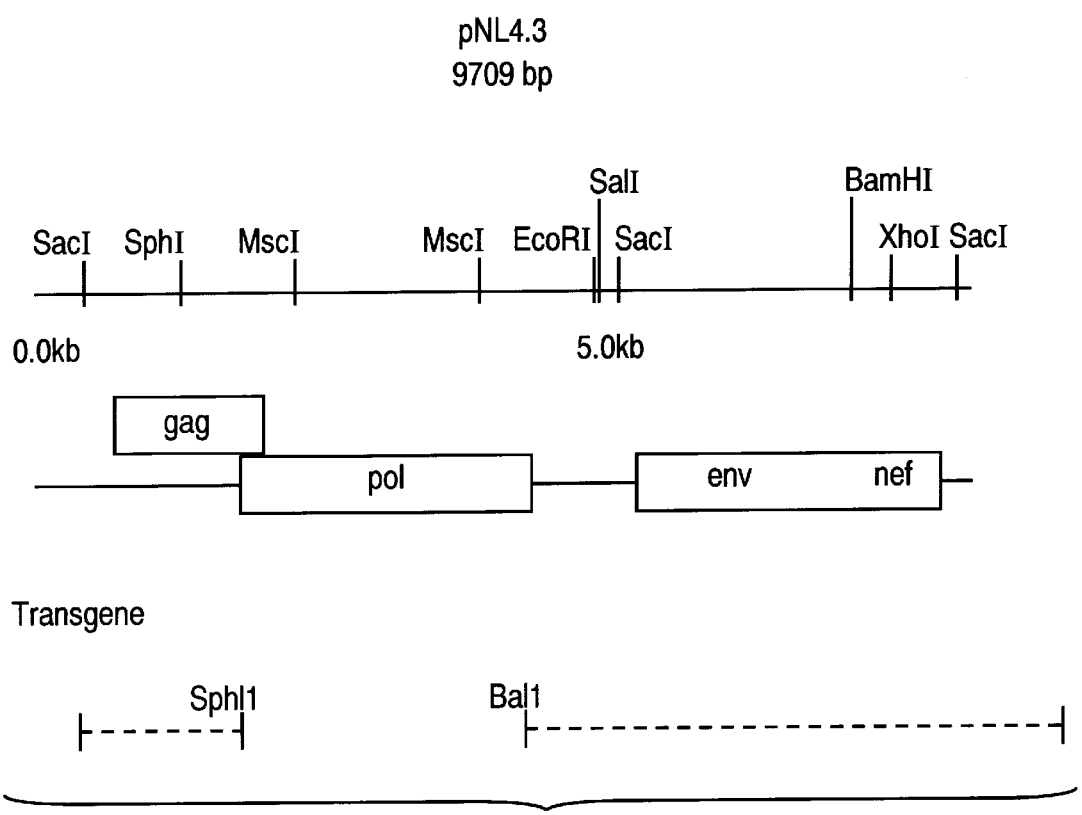
FIG. 1 is a schematic diagram of the HIV-1 proviral DNA used to prepare HIV-1 transgenic rats as described in the Examples.

The invention is based at least in part on the generation of HIV transgenic rats, which develop characteristic AIDS symptoms and that express the HIV envelope protein, gp120.

Definitions

For convenience, the meaning of certain terms and phrases employed in the specification, examples and appended claims are provided below.

"Antigen" refers to a protein, polypeptide, peptide or other molecule, which is capable of eliciting an immune response when administered to a vertebrate.

"Animal line" refers to a group of animals that are direct descendants of one founder animal and which bear one or more transgenes stably integrated into one or more loci in their germline.

A "DNA construct" refers to a DNA molecule comprising a transgene.

"Founder" generally refers to a first transgenic animal, which has been obtained from any of a variety of methods, e.g., pronuclei injection.

"Genome" is intended to include the entire DNA complement of an organism, including the nuclear DNA component, chromosomal or extrachromosomal DNA, as well as the cytoplasmic domain (e.g., mitochondrial DNA). The genome of a eukaryotic organisms, in contrast to bacterial and viral organisms, is usually arranged into chromosomes within the cell nucleus.

"gp-120 is expressed on the surface of a cell" or "a cell expressing gp-120 on its surface" refers to a cell which contains at least one molecule of gp-120 on its surface, preferably at least about 10, at least about 100, at least about 1000, at least about 10,000 or at least about 100,000 gp-120 molecules on its surface. Preferred cells expressing gp-120 are those on which gp-120 can be detected by flow cytometry using an anti-gp120 antibody. Other preferred cells expressing gp-120 are cells which have a biological activity typical of cells having gp-120 on their surface, e.g., interaction with CD4 and/or which are capable of syncytium formation.

"Heterologous DNA", which is used interchangeably with "exogenous DNA" refers to DNA that is not naturally present in the cell.

The term "HIV" is used interchangeably herein with the terms "LAV", "LAV-2", "HTLV-III", and "ARV" to refer to human immunodeficiency virus (HIV). HIV includes both type 1 and type 2 human immunodeficiency viruses and their strains, unless it is used within the context of a specific embodiment related to type 1 or type 2 virus. The terms "HIV-1" and "HIV-2" are used to distinguish the type 1 virus and its strains from the type 2 virus and its strains. The HIV-1 and HIV-2 genomes, and the DNA sequences of HIV-1 and HIV-2, and respective strains are further described herein, as well as in the publication "Human Retrovirus And AIDS 1991", Eds. G. Myer et al., Theoretical Biology and Biophysics, Los Alamos National Laboratory, Los Almos, N. Mex., 87545, USA. Nucleotide sequences of HIV strains can be found in Genbank under the following Accession Nos: 1) HIV-1: K03455, M19921, K02013, M38431, M38429, K02007 and M17449; 2) HIV-2: M30502, J04542, M30895, J04498, M15390, M31113 and L07625 from J. M. Coffin, S. H. Hughes, and H. E. Varmus, "Retroviruses" Cold Spring Harbor Laboratory Press, 1997, p 804). In addition to HIV sequences available from Genbank as described above, HIV sequences can also be found, e.g., in the HIV sequence database publically available at hiv-web.lanl.gov. A map of the HIV-1 genome and transcripts can be found, e.g., in J. M. Coffin, S. H. Hughes, and H. E. Varmus, "Retroviruses" Cold Spring Harbor Laboratory Press, 1997, p803). Set forth in Table 1 is the name and nucleotide location of the major genes of HIV-1 (from Coffin et al., supra pp 802, 804):

TABLE 1

| name | nucleotides | comments |
| --- | --- | --- |
| R | 1–96 | Repeat is a short sequence containing the transactivator response region (TAR, i.e., Tat Responsive) |
| U5 | 97–181 | |
| PBS | 182–199 | |
| gag | 336–1836 | encodes Pr55 Gag |
| pro | 1637–2099 | encodes a Pr160 Gag-Pro-Pol precursor |
| pol | 2102–4640 | pol gene products are synthesized as part of Pr160 |
| vif | 4587–5163 | encodes p23 Vif protein |
| vpr | 5105–5339 | encodes p15 Vpr protein |
| tat | 5377–5591 7925–7968 | encodes p14 Tat protein; binds to the Tat region of R |
| rev | 5516–5591 7925–8197 | encodes p19 Rev protein |
| vpu | 5608–5854 | encodes p16 Vpu protein |
| env | 5771–8339 | encodes the gPr160 Env precursor |
| nef | 8343–8710 | encodes p27 Nef |
| PPT | 8615–8630 | serves as principal primer for plus strand synthesis |
| U3 | 8631–9085 | |
| R | 9086–9181 | |

Amino acid sequences of HIV-1 proteins can also be found in Genbank under the following Accession Nos.(from Coffin et al., supra p 804): gag-P04591; pol-P04585; env-p04578; vif-p03401; vpr-p05926; vpu-p05919; tat-p04608; rev-p04618; and nef-p0460 1. HIV-2 has basically the same molecular organization as HIV-1. However, contrary to HIV-1, HIV-2 contains a gene called vpx, which encodes a 14 kDa protein of unknown function. Another difference is that HIV-2 does not contain the vpu gene, which is present in the HIV-1 genome. Another difference between HIV-1 and HIV-2 is the presence of a large insertion in the HIV-2 rev gene. There are also significant differences between HIV-1 and HIV-2 rev in addition to this insertion.

In addition, a human T cell line that produces HIV is available under ATCC Designation No. CRL-8543. A vector containing the full length HIV-1 genome is available under ATCC Designation No. 53069. DNA encoding specific HIV genes is also available from the ATCC, e.g., a clone of human TAR (HIV) RNA binding protein 1 is available under ATCC Designation No. 107237 and a DNA encoding env-3 from HIV-1 is available under ATCC Designation No. 53072.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. Two DNA sequences are "substantially homologous" or "substantially similar" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the sequences of the present invention. Two amino acid sequences are "substantially homologous" or "substantially similar" when greater than 70% of the amino acids are identical, or functionally identical. Preferably, the similar or homologous sequences are identified by alignment using, for example, the GCG (Genetics Computer Group, Program Manual for the GCG Package, Version 7, Madison, Wis.) pileup program.

An "infectious" virus or virus particle refers to a virus that is capable of replicating and producing new viral particles when it infects an appropriate cell.

An "inbred animal line" is intended to refer to animals which are genetically identical at all endogenous loci.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Lentiviruses" include primate lentiviruses, e.g., human immunodeficiency virus types 1 and 2 (HIV-1/HIV-2); simian immunodeficiency virus (SIV) from Chimpanzee (SIVcpz), Sooty mangabey (SIVsmm), African Green Monkey (SIVagm), Syke's monkey (SIVsyk), Mandrill (SIVmnd) and Macaque (SIVmac). Lentiviruses also include feline lentiviruses, e.g., Feline immunodeficiency virus (FIV); Bovine lentiviruses, e.g., Bovine immunodeficiency virus (BIV); Ovine lentiviruses, e.g., Maedi/Visna virus (MVV) and Caprine arthritis encephalitis virus (CAEV); and Equine lentiviruses, e.g., Equine infectious anemia virus (EIAV). All lentiviruses express at least two additional regulatory proteins (Tat, Rev) in addition to Gag, Pol, and Env proteins. Primate lentiviruses produce other accessory proteins including Nef, Vpr, Vpu, Vpx, and Vif. Generally, lentiviruses are the causative agents of a variety of disease, including, in addition to immunodeficiency, neurological degeneration, and arthritis. Nucleotide sequences of the various lentiviruses can be found in Genbank under the following Accession Nos. (from J. M. Coffin, S. H. Hughes, and H. E. Varmus, "Retroviruses" Cold Spring Harbor Laboratory Press, 199,7 p 804): 1) HIV-1: K03455, M19921, K02013, M3843 1, M38429, K02007 and M17449; 2) HIV-2: M30502, J04542, M30895, J04498, M15390, M31113 and L07625; 3) SIV:M29975, M30931, M58410, M66437, L06042, M33262, M19499, M32741, M31345 and L03295; 4) FIV: M25381, M36968 and U1 1820; 5)BIV. M32690; 6)E1AV: M16575, M87581 and U01866; 6)Visna: M10608, M51543, L06906, M60609 and M60610; 7) CAEV: M33677; and 8) Ovine lentivirus M31646 and M34193. Lentiviral DNA can also be obtained from the American Type Culture Collection (ATCC). For example, feline immunodeficiency virus is available under ATCC Designation No. VR-2333 and VR-3112. Equine infectious anemia virus A is available under ATCC Designation No. VR-778. Caprine arthritis-encephalitis virus is available under ATCC Designation No. VR-905. Visna virus is available under ATCC Designation No. VR-779.

"Nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Non-infectious" virus or virus particle refers to a virus that is incapable of producing new viral particles even when it infects an appropriate cell. A non-infectious human immunodeficiency virus typically has a deletion in gag and/or pol and is thereby incapable of replicating and encapsidating the viral DNA.

"Phenotype" refers to an observable property of an organism (in contrast to the genotype, i.e. genetic composition of the organism).

The terms "protein", "polypeptide" and "peptide" are used interchangeably herein when referring to a gene product.

The term "proviral" DNA refers to a form of a virus that is integrated into the genetic material of a host cell and by replicating with it can be transmitted from one cell generation to the next.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that inhibit viral gene expression, virus replication, and/or viral production.

DNA "regulatory elements" include transcriptional and translational control elements, such as promoters, enhancers, silencers, terminators, and the like, that provide for translation or expression of a nucleic acid. In eukaryotic cells, polyadenylation signals are control sequences.

The phrase "therapeutically effective amount" as used herein refers to an amount sufficient to improve by at least about 15 percent, preferably by at least about 50 percent, more preferably by at least about 90 percent, and most preferably by about 100% (i.e., cure) a medical condition or symptoms thereof in a subject. Alternatively the therapeutically effective amount can be an amount sufficient to reduce by at least about 15 percent, preferably by at least about 50 percent, more preferably by at least about 90 percent, and most preferably by about 100% the viral load, expression of a gene, e.g, a viral gene, or viral replication.

A cell has been "transfected" by exogenous or heterologous DNA when such DNA has been introduced into the cell. A cell has been "transformed" by exogenous or heterologous DNA when the transfected DNA effects a phenotypic change. Preferably, the transforming DNA should be integrated (covalently linked) into chromosomal DNA making up the genome of the cell.

The term "transgene" broadly refers to any nucleic acid that is introduced into an animal's genome, including but not limited to genes or DNA having sequences which are perhaps not normally present in the genome, genes which are present, but not normally transcribed and translated ("expressed") in a given genome, or any other gene or DNA which one desires to introduce into the genome. This may include genes which may normally be present in the non-transgenic genome but which one desires to have altered in expression, or which one desires to introduce in an altered or variant form. A transgene can include one or more transcriptional regulatory sequences and any other nucleic acid, such as introns, that may be necessary for optimal expression of a selected nucleic acid. A preferred transgene of the invention is a viral transgene, e.g., a lentiviral transgene. A transgene can be as few as a couple of nucleotides long, but is preferably at least about 50, 100, 150, 200, 250, 300, 350, 400, or 500 nucleotides long or even longer and can be, e.g., an entire viral genome. A transgene can be coding or non-coding sequences, or a combination thereof A transgene usually comprises a regulatory element that is capable of driving the expression of one or more transgenes under appropriate conditions. A "lentiviral transgene" refers to a nucleic acid comprising a nucleotide sequence encoding at least one lentiviral protein or biologically active portion thereof. An "HIV transgene" refers to a nucleic acid comprising a nucleotide sequence encoding at least one HIV protein or biologically active portion thereof A "transgenic animal" refers to any animal, preferably a non-human mammal (e.g. mouse, rat, rabbit, squirrel, hamster, rabbits, guinea pigs, pigs, micro-pigs, prairie, baboons, squirrel monkeys and chimpanzees, etc), bird or an amphibian, in which one or more cells contain heterologous nucleic acid introduced by way of human intervention, such as by transgenic techniques well known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a viral gene. However, transgenic animals in which the transgene is silent are also contemplated, as for example, the FLP or CRE recombinase dependent constructs.

The term "treating" as used herein is intended to encompass curing as well as ameliorating at least one symptom of the condition or disease.

A "vaccine" refers to a preparation containing at least one lentiviral antigen, which can be administered to a subject to produce or artificially increase immunity to a disease, which is caused by or contributed to by a lentivirus. In addition to the at least one antigen, the vaccine can optionally comprise a pharmaceutically acceptable carrier and/or an adjuvant.

The term "wild-type viral gene or genome" refers to a viral gene or genome as it is found in nature, i.e., which has not been manipulated by man. Thus, there may exist several wild-type genomes for each type of virus.

Lentiviral Transgenes and Trans genic Animals Produced Therefrom

The invention provides for transgenic non-human animals comprising a lentivirus transgene, (e.g., an HIV transgene). The lentiviral construct can be an infectious virus, which is capable of replicating and producing viral particles. An example of an infectious HIV-1 DNA includes the DNA construct referred to as pNL4-3 (Adachi et al. (1986) J. Virol. 59:284 and Leonard et al. (1988) Science 242:1665; Genbank Accession No. M19921). Another infectious HIV-1 proviral construct is pNL4-32 (Strebel et al. (1987) J. Virol. 328:728 and Leonard et al., supra). Transgenic non-human animals made with infectious HIV transgenes, alone or in conjunction with a transgene encoding a CD4 receptor (e.g. the human CD4 receptor) and/or an HIV co-receptor transgene (e.g. CCR5 or CXCR4) can produce infectious viral particles, which infect host cells, and therefore are particularly preferred for developing effective HIV vaccines and therapeutics.

Non-human transgenic animals, which are noninfectious and therefore potentially safer for use, can be generated using transgenes comprised of non-infectious viral DNA, i.e., viral DNA which does not result in the formation of viral particles upon infection of a host cell. For example, a non-infectious viral DNA can have a deletion or other type of mutation in any coding region or regulatory region sufficient to impair viral nucleic acid replication, and/or assembly of virions. The deletion can inhibit production of, or inactivate, one or more of the proteins selected from the group consisting of a nucleocapsid-core factor (e.g., gag), reverse transcriptase, protease, integrase, ribonuclease, and transcriptional activator (e.g., tat). An example of an HIV-1 provirus that is non-infectious is the pNL4-3 :dI443 vector, which is derived from the infectious pNL4-3 vector by deletion of a 3.1 kb sequence overlapping gag and pol (sequences between the SphI and BalI sites at bases 1443–4556), but containing env and the other accessory genes tat, nef, vif, vpr, and vpu, together with the 5' and 3' long terminal repeats (LTRs). As described in the following Examples, pNL4-3:d1443 has been used to produce transgenic rats, which model human AIDS.

Other non-infectious HIV DNA can be obtained by deleting portions of one or both LTRs. For example, the HIV DNA sequence can be prepared by digesting a plasmid clone containing the DNA sequence of HIV-1 with a restriction enzyme that cleaves the HIV proviral DNA sequence at sites proximal to its 5' and 3' ends, thereby removing essential controlling sequences, to yield a proviral DNA sequence truncated at both ends, so that the eventual RNA expression from the cleaved fragment is rendered non-infectious, but still includes those elements required for the eventual production of at least some viral proteins. In other words, the HIV genome is modified to lack the sequences necessary for reverse transcription, integration and/or transcription. The extent to which the 5' and 3' ends must be truncated to render the RNA non-infectious can be determined by standard methods (e.g. by transforming the fragment so obtained into a genomic equivalent of HIV-1 and testing the resulting virus for cytopathic activity). As an example, the SacI restriction enzyme can be used to cleave the pBH10 plasmid [B. H. Hahn et al., Nature, 312, 166 (1984)] to yield an HIV-1 genome deleted of the 5' LTR and/or a portion of its 3' LTR. Non-infectious HIV proviral DNA deleted 5' and/or 3' are further described in U.S. Pat. No. 5,574,206 by Jolicoeur.

Another method for obtaining a non-infectious HIV proviral DNA sequence involves truncating the HIV genomic DNA fragment from its 5' end to a point on the untranslated 5' leader sequence located between about 50 nucleotides downstream from the 5' LTR, but not including the nucleotide marking the beginning of the splice donor sequence; and truncating the same HIV DNA fragment from its 3' end sequence to a point located downstream of the nef gene, so that the complete encoding sequence of the nef gene is retained and sequences required for virus replication (i.e. the U5, R and part of the U3 sequences) are deleted.

Transgenic animals exhibiting tissue specific expression can be generated, for example, by inserting a tissue specific regulatory element, such as an enhancer, into the viral transgene. For example, one of the LTRs or a portion thereof can be replaced with another promoter and/or enhancer, e.g., a CMV or a Moloney murine leukemia virus (MLV) promoter and/or enhancer. For example, the proviral HIV DNA is pNL4-3, in which the two NF-κB binding motifs of the HIV core enhancer sequences from the Moloney murine Leukemia Virus (Mo-MuLV) LTR by M13 mutagenesis (deleting nucleotides −129 to −74, with respect to the HIV mRNA cap site and replacing them with nucleotides −365 to −40 from the Mo-MuLV). This construct is further described (as pHm4-3) in Dickie et al. (1996) AIDS Res. Human Retroviruses 12:177, which also describes transgenic mice containing this construct.

An LTR of a proviral genome, e.g, HIV proviral genome, can also be replaced with a mouse mammary tumor virus (MMTV) LTR, which is known to be tissue specific toward various epithelial and hematopoietic tissues, some of which naturally support lentivirus (and especially HIV) replication. (for an example of such a construct, see, e.g., U.S. Pat. No. 5,574,206 issued Nov. 12, 1996 to Jolicoeur).

Alternatively, non-human transgenic animals that only express HIV transgenes in the brain can be generated using brain specific promoters (e.g. myelin basic protein (MBP) promoter, the neurofilament protein (NF-L) promoter, the gonadotropin-releasing hormone promoter, the vasopressin promoter and the neuron-specific enolase promoter, see So Forss-Petter et al., Neuron, 5, 187, (1990). Such animals can provide a useful in vivo model to evaluate the ability of a potential anti-HIV drug to cross the blood-brain barrier. Other target cells for which specific promoters can be used are, for example, macrophages, T cells and B cells. Other tissue specific promoters are well-known in the art, see e.g. R.Jaenisch, Science, 240, 1468 (1988).

Non-human transgenic animals containing an inducible lentiviral transgene (infectious or noninfectious) can be generated using inducible regulatory elements (e.g. metallothionein promoter), which are well-known in the art. Lentiviral gene expression can then be initiated in these animals by administering to the animal a compound which induces gene expression (e.g. heavy metals). Another preferred inducible system comprises a tetracycline-inducible transcriptional activator (U.S. Pat. No. 5,654,168 issued Aug. 5, 1997 to Bujard and Gossen and U.S. Pat. No. 5,650,298 issued Jul. 22, 1997 to Bujard et al.).

Double, triple or multimeric transgenic animals, comprise at least one other transgene in addition to the lentiviral transgene. In a preferred embodiment, the animal comprises an HIV transgene and a transgene encoding human CD4 protein or a portion thereof sufficient for HIV infection of target cells. The nucleotide sequence of cDNA encoding human CD4 can be found, e.g., in Maddon et al. (1985) Cell 42:93. Mice containing a CD4 transgene are described, e.g., in Wang et al., (1994) Eur. J. Immunol., 24: 1553. A human CD4 transgenic rabbit has been described, e.g, in PCT application No. PCT/FR93/00598 (WO 94/00568) by Mehtali et al.

In another preferred embodiment, the animal comprises an HIV transgene and a transgene, which expresses a coreceptor (e.g. CCR5 or CXCR4). In a further preferred embodiment, the animal comprises an HIV transgene and a transgene (e.g. mutant gene), which is involved in a disease or condition that is associated with AIDS (e.g. hypertension, Kaposi's sarcoma, cachexia, etc.). For example, the transgenic animals of the invention can be crossed with hypertensive rats of the transgenic rat strain TGR(mREN2)27 harboring the murine Ren-2 gene or transgenic rats comprising a transgene encoding human angiotensinogen and/or human renin (U.S. Pat. No. 5,731,489). These transgenic rats develop fulminant hypertension at an early age despite low levels of renin in plasma and kidney (described in, e.g., Lee et al. (1996) Am J Physiol 270: E919).

Where one or more genes encoding a protein are used as transgenes, it may be desirable to operably link the gene to an appropriate regulatory element, which will allow expression of the transgene. Regulatory elements, e.g., promoters, enhancers, (e.g. inducible or constitutive) or polyadenylation signals are well known in the art. Regulatory sequences can be endogenous regulatory sequences, i.e., regulatory sequences from the same animal species as that in which it is introduced as a transgene. The regulatory sequences can also be the natural regulatory sequence of the gene that is used as a transgene. Accordingly, regulatory elements for a CD4 transgene can be the natural CD4 regulatory elements and can include 5' flanking sequence of the CD4 gene comprising promoter and enhancer sequences.

Alternatively, a transgene can be placed under the control of an exogenous regulatory element, i.e. a regulatory element, which is not the normal regulatory element of the transgene. For example, a human CD4 transgene can be placed under the control of a promoter that is functional in specific cell types, e.g., in T lymphocytes. An exemplary promoter for use in transgenic rats is the rat CD2 promoter. Alternatively, the transcriptional regulatory element can be a viral promoter, e.g, the MMTV LTR.

The transgene also preferably contains a polyadenylation signal (poly A addition sequence), which can comprise one or a tandem of two to four of the known poly A addition signal sequences, such as those derived from the SV40 genome, the casein 3' untranslated region or other 3' untranslated sequences known in the art. A convenient and readily available source for the poly A addition signal is the commercially available pSV2neo vector from which the SV40 poly A addition signal sequence can be cleaved. The transgene can be prepared using techniques known in the art; for example see J. Sambrook et al., "Molecular Cloning: A Laboratory Manual", 2nd ed, Vols 1 to 3, Cold Spring Harbor Laboratory Press, Cold Spring Harbor, N.Y., USA, 1989.

Constructs for use as transgenes can first be tested for expression in cell lines. Where the transcriptional control elements in the construct are those from a virus, e.g., HIV, it may be desirable to use a test cell line of the same type as that which is naturally infected by the virus. For example, when testing a construct derived from an HIV provirus, it may be desirable to use a cell line in which HIV is expressed and is preferably capable of replicating, e.g., T cell lines. Examples of cell lines in which HIV is known to replicate include primary human PBMC, isolated macrophages, isolated CD4+ T cells and cultured human cell lines, such as HeLa and H9. Expression of the transgene and/or production of viral particles can be detected as further set forth herein.

Production of transgenic non-human animals

In general, transgenic animal lines can be obtained by generating transgenic animals having incorporated into their genome at least one transgene, selecting at least one founder from these animals and breeding the founder or founders to establish at least one line of transgenic animals having the selected transgene incorporated into their genome.

Animals for obtaining eggs or other nucleated cells (e.g. embryonic stem cells) for generating transgenic animals can be obtained from standard commercial sources such as Charles River Laboratories (Wilmington, Mass.), Taconic (Germantown, N.Y.), Harlan Sprague Dawley (Indianapolis, Ind.).

Eggs can be obtained from suitable animals, e.g., by flushing from the oviduct or using techniques described in U.S. Pat. No. 5,489,742 issued Feb. 6, 1996 to Hammer and Taurog; U.S. Pat. No. 5,625,125 issued on Apr. 29, 1997 to Bennett et al.; Gordon et al., 1980, Proc. Natl. Acad. Sci. USA 77:7380–7384; Gordon & Ruddle, 1981, Science 214: 1244–1246; U.S. Pat. No. 4,873,191 to T. E. Wagner and P. C. Hoppe; U.S. Pat. No. 5,604,131; Armstrong, et al. (1988) J. of Reproduction, 39:511 or PCT application No. PCT/FR93/00598 (WO 94/00568) by Mehtali et al. Preferably, the female is subjected to hormonal conditions effective to promote superovulation prior to obtaining the eggs.

Many techniques can be used to introduce DNA into an egg or other nucleated cell, including in vitro fertilization using sperm as a carrier of exogenous DNA ("sperm-mediated gene transfer", e.g., Lavitrano et al., 1989, Cell 57: 717–723), microinjection, gene targeting (Thompson et al., 1989, Cell 56: 313–321), electroporation (Lo, 1983, Mol. Cell. Biol. 3: 1803–1814), transfection, or retrovirus mediated gene transfer (Van der Putten et al., 1985, Proc. Natl. Acad. Sci. USA 82: 6148–6152). For a review of such techniques, see Gordon (1989), Transgenic Animals, Intl. Rev. Cytol. 115:171–229.

Except for sperm-mediated gene transfer, eggs should be fertilized in conjunction with (before, during or after) other transgene transfer techniques. A preferred method for fertilizing eggs is by breeding the female with a fertile male. However, eggs can also be fertilized by in vitro fertilization techniques.

Fertilized, transgene containing eggs can than be transferred to pseudopregnant animals, also termed "foster mother animals", using suitable techniques. Pseudopregnant animals can be obtained, for example, by placing 40–80 day old female animals, which are more than 8 weeks of age, in cages with infertile males, e.g., vasectomized males. The next morning females are checked for vaginal plugs. Females who have mated with vasectomized males are held aside until the time of transfer.

Recipient females can be synchronized, e.g. using GNRH agonist (GnRH-a): des-gly10, (D-Ala6)-LH-RH Ethylamide, Sigma Chemical Co., St. Louis, Mo. Alternatively, a unilateral pregnancy can be achieved by a brief surgical procedure involving the "peeling" away of the bursa membrane on the left uterine horn. Injected embryos can then be transferred to the left uterine horn via the infundibulum. Potential transgenic founders can typically be identified immediately at birth from the endogenous litter mates. For generating transgenic animals from embryonic stem cells, see e.g. Teratocarcinomas and embryonic stem cells, a practical approach, ed. E. J. Robertson, (IRL Press 1987) or in Potter et al Proc. Natl. Acad. Sci. USA 81, 7161 (1984), the teachings of which are incorporated herein by reference.

Founders that express the gene can then bred to establish a transgenic line. Accordingly, founder animals can be bred, inbred, crossbred or outbred to produce colonies of animals of the present invention. Animals comprising multiple transgenes can be generated by crossing different founder animals (e.g. an HIV transgenic animal and a transgenic animal, which expresses human CD4), as well as by introducing multiple transgenes into an egg or embryonic cell as described above. Furthermore, embryos from A-transgenic animals can be stored as frozen embryos, which are thawed and implanted into pseudo-pregnant animals when needed (See e.g. Hirabayashi et al. (1997) Exp Anim 46: 111 and Anzai (1994) Jikken Dobutsu 43: 247).

The present invention provides for transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In particular, the expression of the gag protein (p55), the gag protein cleavage products p24 and p17, the envelope glycoprotein (gp160) and the envelope protein cleavage product gp120 can be detected using specific probes and/or antibodies. At least some of these antibodies are commercially available. For example, monospecific anti-gp120 reagent can be obtained, e.g., from Biochorm, Seromed Ref. D7324. Sheep anti-gp120 serum of HIV-1 can also be obtained from the AIDS Research and Reference Program (catalog no. 192), National Institutes of Health, Bethesda, Md. Human monoclonal anti-gp120 antibodies are also described in U.S. Pat. No. 5,695,927 issued Dec. 7, 1997 to Masuho et al.

Animal tissue can also be analyzed directly, e.g., by preparing tissue sections. In some embodiments, it is preferable to fix the tissue, e.g., with paraformaldehyde or formalin. Tissue sections can be prepared frozen, or can be paraffin embedded. Slides of animal tissue can be used for immunohistochemistry, in vitro hybridization or for regular histology, e.g., hematoxylin and eosin staining.

Virus can be quantitated by reverse transcriptase (RT) activity, as is well-known in the art. A change in viral load can also be determined by quantitative assays for plasma HIV RNA using quantitative RT-PCR as described, e.g, in Van Gemen et al. (1994) J. Viro. Methods 49:157; Chen et al. (1992) AIDS 6:533. Alternatively, viral load can be determined by assays for viral production from isolated PBMCs. Viral production from PBMCs is determined by cocultruring PBMCs from the subject with H9 cells and subsequent measurement of HIV titers using an ELISA assay for p24 antigen levels (Popovic et al. (1984) Science 204:497; PCT/US97/11202 (W097/49373) by Gallo et al.). To identify lymphoid cell types expressing viral RNA, peritoneal inflammatory macrophages derived from the transgenic animals can be cultured ex vivo and examined by Northern blot analysis.

Disease Models and Drug Screening Assays

The invention further provides methods for identifying (screening) or for determining the safety and/or efficacy of lentivirus therapeutics, i.e. compounds which are useful for treating and/or preventing the development of diseases or conditions, which are caused by, or contributed to by lentiviral infection (e.g. AIDS). In addition the assays are useful for further improving known anti-viral compounds, e.g, by modifying their structure to increase their stability and/or activity and/or toxicity.

In vitro cellular assays

Cells from the transgenic animals of the invention can be established in culture and immortalized to establish cell lines. For example, immortalized cell lines can be established from the livers of transgenic rats, as described in Bulera et al. (1997) Hepatology 25: 1192. Cell lines from other types of cells can be established according to methods known in the art."

In one cell-based assay, cells expressing a lentivirus protein (e.g. receptor) on the outer surface of its cellular membrane can be incubated in the presence of a test compound alone or in the presence of a test compound and a lentivirus protein binding partner (e.g. a receptor ligand) and the interaction between the test compound and the lentivirus protein or between the lentivirus binding partner (preferably tagged) and the lentivirus protein can be detected, e.g., using a microphysiometer (McConnell et al. (1992) Science 257:1906). An interaction between the lentivirus protein and either the test compound or the lentivirus protein binding partner can be detected, (e.g. with a microphysiometer as a change in the acidification of the medium). This assay system thus provides a means of identifying molecular antagonists which, for example, function by interfering with a lentivirus ligand-receptor interaction, as well as molecular agonist which, for example, function by activating a lentivirus protein (e.g. receptor).

Cell based assays can also be used to identify compounds which modulate expression of a lentivirus gene, modulate translation of a lentivirus mRNA, or which modulate the stability of a lentivirus mRNA or protein. Accordingly, a cell which is capable of expressing a particular lentivirus protein can be incubated with a test compound and the amount of the lentivirus protein produced in the cell medium can be measured and compared to that produced from a cell which has not been contacted with the test compound. The specificity of the compound for regulating the expression of the particular lentivirus gene can be confirmed by various control analyses, e.g., measuring the expression of one or more control genes. This type of cellular assay can be particularly useful for determining the efficacy of antisense molecules or ribozymes.

In another embodiment, the effect of a test compound on transcription of a particular lentivirus gene can be determined by transfection experiments using a reporter gene, which is operatively linked to at least a portion of the promoter of a lentivirus gene. A promoter region of a gene can be isolated, e.g., from a genomic library according to methods known in the art. The reporter gene can be any gene encoding a protein which is readily quantifiable, e.g, the luciferase or CAT gene. Such reporter gene are well known in the art.

In vivo assays in transgenic animals

In addition to providing cells for in vitro assays, the transgenic animals themselves can be used in in vivo assays to identify lentiviral therapeutics. For example, the animals can be used in assays to identify compounds which reduce or inhibit any phase of the lentiviral life cycle, e.g., expression of one or more viral genes, activity of one or more viral proteins, glycosylation of one or more viral proteins, processing of one or more viral proteins, viral replication, assembly of virions, and/or budding of infectious virions.

In an exemplary embodiment, the assay comprises administering a test compound to a transgenic animal of the invention and comparing a phenotypic change in the animal relative to a transgenic animal which has not received the test compound. For example, where the animal is an HIV transgenic animal, the phenotypic change can be the amelioration in an AIDS related complex (ARC), cataracts, inflammatory lesions in the central nervous system (CNV), a mild kidney sclerotic lesion, or a skin lesion, such as psoratic dermatitis, hyperkerstotic lesions, Kaposi's sarcoma or cachexia. The effect of a compound on inhibition of Kaposi's sarcoma can be determined, as described, e.g., in PCT/US97/11202 (WO97/49373) by Gallo et al. These and other HIV related symptoms or phenotypes are further described in Leonard et al. (1988) Science 242:1665.

In yet another embodiment, the phenotypic change is the number of CD4+ T cells or the ratio of CD4+ T cells versus CD8+ T cells. In HIV infected humans as well as in HIV transgenic mice, analysis of lymph nodes indicate that the number of CD4+ T cells decreases and the number of CD8+ T cells increases. Numbers of CD4+ and CD8+ T cells can be determined, for example, by indirect immunofluorescence and flow cytometry, as described, e.g., in Santoro et al., supra.

Alternatively, a phenotypic change, e.g. a change in the expression level of an HIV gene can be monitored. The HIV RNA can be selected from the group consisting of gag mRNA, gag-pro-pol mRNA, vif mRNA, vpr mRNA, tat mRNA, rev mRNA, vpu/env mRNA, nef mRNA, and vpx mRNA. The HIV protein can be selected from the group consisting of Pr55 Gag and fragments thereof (p17 MA, p24 CA, p7 NC, p1, p9, p6, and p2), Pr160 Gag-Pro-Pol, and fragments thereof (p10 PR, p51 RT, p66 RT, p32 IN), p23 Vif, p15 Vpr, p14 Tat, p19 Rev, p16 Vpu, gPr 160 Env or fragments thereof (gp120 SU and gp41TM), p27 Nef, and p14 Vpx. The level of any of these mRNAs or proteins can be determined in cells from a tissue sample, such as a skin biopsy, as described in, e.g., PCT/US97/11202 (W097/49373) by Gallo et al. Quantitation of HIV mRNA and protein is further described elsewhere herein and also in, e.g., Dickie et al. (1996) AIDS Res. Human Retroviruses 12:1103. In a preferred embodiment, the level of gp120 on the surface of PBMC is determined. This can be done, as described in the examples, e.g., by immunofluorescence on PBMC obtained from the animals.

For example, the proteins expressed in the cells of a transgenic animal of the invention may include processed gag proteins resulting from the cleavage of the HIV-1 encoded gag-pol gene, the cleavage being effected by the HIV-1 encoded protease. Thus, in one embodiment, the invention provides a method for evaluating a test compound as a potential HIV-1 protease inhibitor. In an exemplary embodiment, the method involves: (a) administering a test compound to the transgenic animal, and (b) examining the effect of the test compound on the expressed gag proteins in the animal by monitoring the expression levels of the proteins or RNAs. The presence of the RNA transcript and the presence or decrease (or inhibition) of the processed proteins in the cells serves as a means for evaluating HIV protease inhibitors.

Likewise, since the presence of the gag and envelope proteins in the fluid and tissues of the transgenic animal denotes that the HIV regulatory protein, rev, is expressed, the present invention provides a method for evaluating a test compound as a potential inhibitor of rev function. In an exemplary embodiment, the method involves: (a) administering a test compound to the transgenic animal, and (b) examining the effect of the test compound on the expressed gag and envelope proteins and the gag protein cleavage products in the animal by monitoring the expression levels thereof A further phenotypic change is the production level or rate of viral particles in the serum and/or tissue of the animal. This can be determined, e.g., by determining reverse transcriptase (RT activity) or viral load as described elsewhere herein as well as in PCT/US97/11202 (WO97/49373) by Gallo et al., such as by determining p24 antigen.

Yet another phenotypic change, which can indicate HIV infection or AIDS progression is the production of inflammatory cytokines such as IL-6, IL-8 and TNF-α; thus, efficacy of a compound as an anti-HIV therapeutic can be assessed by ELISA tests for the reduction of serum levels of any or all of these cytokines.

A vaccine can be tested by administering a test antigen to a transgenic animal of the invention. The animal can optionally be boosted with the same or a different antigen. The production of viral particles or expression of viral proteins is then measured at various times following the administration of the test vaccine. A decrease in the amount of viral particles produced or viral expression will indicate that the test vaccine is efficient in reducing or inhibiting viral production and/or expression. The amount of antibody produced by the animal in response to the vaccine antigen can also be determined according to methods known in the art and provides a relative indication of the immunogenicity of the particular antigen.

Therapeutic and Prophylactic Compounds

Compounds identified above as being useful for preventing lentiviral infection and/or treating a lentiviral disease, can be, e.g. a nucleic acid (e.g DNA, RNA or PNA), protein, peptide, peptidomimetic, small molecule, or derivative thereof Preferred compounds are capable of binding to, and inhibiting transcription, translation or processing of a lentiviral RNA or protein. Examples include antisense, ribozyme or triplex nucleic acids, small molecule ligands, antibody or antibody-like binding fragments). Alternative compounds are competitive inhibitors of a protein involved in lentiviral infection, such as a portion of human CD4 sufficient to bind to gp120 and interfere with binding of gp120 proteins on the surface of an infected cell or on the surface of a viral particle to a human CD4 molecule on the surface of cells.

Toxicity and therapeutic efficacy of such compounds can be determined by standard pharmaceutical procedures in cell cultures or experimental animals, e.g., for determining the Ld5O (The Dose Lethal To 50% Of The Population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possiblity of local noninvasive delivery of drugs over an extended period of time. This technology utilizes microspheres of precapillary size which can be injected via a coronary chatheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives, in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In situations in which the therapeutic is a gene, a gene delivery system can be introduced into a patient by any of a number of methods, each of which is familiar in the art. For instance, a pharmaceutical preparation of the gene delivery system can be introduced systemically, e.g., by intravenous injection, and specific transduction of the fir, protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). A therapeutic gene, such as a gene encoding an antisense RNA or a ribozyme can be delivered in a gene therapy construct by electroporation using techniques described, for example, by Dev et al. ((1994) Cancer Treat Rev 20:105–115).

A gene therapy preparation can consist essentially of a gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Preparation of an HIV-1 transgenic rat

A transgenic rat containing a proviral HIV-1 DNA, i.e., plasmid pNL4-3:d1443, was prepared as follows.

The HIV-1 proviral DNA in the plasmid pNL4-3:d1443 (represented in FIG. 1) is an artificial recombination of two strains. The 5' half of pNL4-3 is the viral isolate NY5 and the 3' half is the viral isolate LAV-1; the recombination splice occurred at the EcoRI site at nucleotide 5743 base 1 being the most 5' nucleotide of the LTR). The DNA used for the construction of the transgenic rat included a deletion of sequence between the BalI and SphI sites (nucleotides 1443–4551), thereby deleting the gag and pol genes. The construct included both the 5' and 3' LTRs and open reading frames for the viral genes, env, tat, rev, nef, vif, vpr, and vpu. The upstream 5' splice acceptor site is left intact. Approximately 1 kb of human flanking sequence is present at both ends. Plasmid pNL4-3 has been described, e.g., in Leonard et al. (1988) Science 242:1665, illustrating the use of this plasmid for the preparation of a transgenic mouse.

Specific pathogen-free inbred Fischer F-344/CrlBR (F344) rats, and outbred Sprague-Dawley (SD) rats, were purchased from Charles River Laboratories, Boston, Mass. Animals were maintained in accordance with institutional guidelines.

Three week old Fisher 344 (F344) female rats (90–120 g) were superovulated according to Methods in Molecular Biology Vol. 18, Transgenesis Techniques, edited by David Murphy and David Carter, Humana Press pp 253–256. Briefly, the female rats were injected intraperitoneally with 0.2 IU/g body weight of pregnant mare serum gonadotropin (PMSG), followed 46–48 hours later with an intraperitoneal injection of 0.2 IU/g body weight of human chorionic gonadotropin (HCG). Each female was then placed in a cage with a stud male. On the morning of the next day, a check was made for copulatory plugs or vaginal smears were performed to check for sperm in the lavage. At 12:00 that day, fertilized one-cell eggs were flushed from the oviducts of females exhibiting either a vaginal plug or sperm in vaginal lavage fluid. The method for collecting fertilized eggs was identical to that previously described for mice (Hogan et al. 1994 and Murphy et al. 1993). Two types of culture media were used for in vitro manipulations of rat embryos. M16 was used for maintaining the eggs at 37° C. gassed with 5% $CO_2$. M2 media was used for in vitro manipulations outside the $CO_2$ incubator for periods less than 30 minutes. Eggs were collected from the ampulla in M2 media containing 300 migcrograms/ml of hyaluronidase. Following removal of the cumulus cells, eggs were washed twice in fresh M2 and transferred to $CO_2$ equilibrated M16 and incubated at 37° C. until required for microinjection.

Pseudopregnant rats were obtained as follows. Female SD rats, at least 8 weeks of age, were maintained on a 12 hour day and 12 hour night cycle so that they ovulate and mate every 4 days. The stage of estrous was determined prior to placing them with vasectomized rats. Sexually mature SD females were anasthetized with Methozyflurane, their vagina flushed and the contents dried and stained with a modified Wright's stain (e.g., Dip-Quick). The vaginal contents were examined at 40× magnification and each female was staged as to their position in the estrous cycle. SD females found to be proestrous were placed with vasectomized SD males, on day 0 by 18:00 hr to generate pseudopregnant recipients.

Vasectomized male rats were obtained by a surgical procedure (Hogan et al., supra). Male rates were anasthetized with 60 mg/kg Ketamine and 7.5 mg/kg Xylazine. The abdomen was shaved and cleaned and the body wall incised and the left and right vas deferens were cauterized. The body wall was then closed with wound clips and the rat caged individually in a warm place until recovered.

Microinjection of Fisher 344 X Sprague Dawley eggs and transfer to day one pseudopregnant Sprague-Dawley females were carried out as follows. For injection, the eggs were transferred to M2 medium. Eggs were sequentially held in place by a blunt pipet (outside diameter about 100 p) while the tip of the injector pipet was inserted through the zona pellucida and vitellus and into one of the pronuclei. The DNA solution consisting of plasmid pNL4-3: d1443 at a concentration of 2 ng/ml in the injector pipet was slowly discharged by using a 100 µl Hamilton syringe connected to a micrometer. The injector pipet was filled with silicone oil except for the DNA solution. After injection, the eggs were transferred to the oviducts of pseudopregnant Sprague-Dawley female rats. The procedure was identical to that described for mice (E. Lacy et al., Manipulating the Mouse Embryo, Cold Spring Harbor Press, N.Y. 1994; and Methods in Molecular Biology Vol. 18, Transgenesis Techniques, edited by David Murphy and David Carter, Humana Press). Briefly, the recipient was anesthetized as previously described and the oviducts exteriorized by a surgical incision made at the level of the paralumbar fossa. Approximately 15–30 embryos were transferred per recipient. The body wall was then closed and the recipient was kept warm until recovery.

Potential founder transgenic rats were initially identified by PCR and/or by restriction enzyme digestion and Southern blot analysis. DNA for PCR or Southern blot analysis was obtained from 2–3 weeks old rat tail tips as per modification of the procedure of Hogan et al. (E. Lacy et al., Manipulating the Mouse Embryo, Cold Spring Harbor Press, N.Y. 1994). Approximately, 1 cm long rat tail tips were excised with a sterile scalpel following anesthesia with 0.02ml SQ of Lidocaine-HCL. Bleeding was controlled with silver nitrate. Following tail tip amputations, rats received Phenylbutazone 50 mg/kg, intraperitoneally as needed for pain. A Quiagen kit was used to extract DNA from tail tips.

Identification and quantitation of transgenes was determined in the founder animals and their progeny by Southern blot analysis of genomic DNA first amplified by PCR Two primers (SK68 (5' AGC AGC AGG AAG CAC TAT GG; SEQ ID NO: 4) and SK69 (5° CCA GAC TGT GAG TTG CAA CAG; SEQ ID NO: 5) were used to specifically amplify a 141 bp region from HIV-1 env by PCR-Southern blot hybridization with a $^{32}p$ labeled 1.2 kb HindIII Nef cDNA fragment was used to confirm the identification of positive animals. Rats positive for the transgenic construct are referred to as "TgN(pNL43d14) FO1 MBC/IHV TG-1" rats. One female Sprague dawley x Fisher 344/NHsd F1 rat was found to carry the HIV transgene. This founder produced many hemizygous offspring and brother-sister matings produced further offspring.

Southern blot hybridization and PCR analysis indicates that copies of the proviral HIV genome are inserted in either 3–6 copies or 6–12 copies in the genome. It is likely that the transgene is inserted on two different chromosomes, resulting in transgenic animals having 3–6 copies or 6–12 copies, depending on whether they have the two chromosomes carrying the transgene or only one. It is believed that the number of copies of the transgene correlates with the degree of certain characteristics of the phenotype of the animal, in particular with the degree of cataracts (light verus heavy cataracts).

Example 2

Phenotype of the HIV transgenic rat

The female founder rat, TG-1, has cataracts in both eyes and a small red circular lesion at the base of the tail. TG-1 was mated with a normal Sprague Dawley male to produce the $F_1$ generation. The $F_1$ offsprings had cataracts that varied from a high degree of opacity to a faint one. The cataracts were supplied with a large number of blood vessels (highly vascular). Transgenic animals had bilateral cataracts at birth. Two phenotypes could be distinguished: one phenotype which consisted of heavy, dark cataracts, and the other consisted of light, milder cataracts.

In addition, at the time of weaning, most animals developed a focal skin lesion at the base of the tail. Of the 10 in the first litter three had red lesions at the base of the tail, all were females. Subsequent offsprings have also demonstrated that a few males have the red lesion. Mating of this phenotype produce offsprings with more severe skin lesions that cover the length of the tail and the offsprings were smaller, especially the females. Early pregnancy in these animals caused the lesions to disappear and return later in pregnancy and fully returned at partituation. The severe skin lesion phenotype were smaller, had a larger amount of proteins in urine, increased BUN and a higher alkaline urine. Skin lesions were that of psoratic dermatitis and hyperkerastotic lesions, mild kidney sclerotic lesions, and inflammatory lesions in the CNS. Thus, the HIV transgenic rat of the invention displays many of the pathology seen in humans with HIV, including retarded growth, CNS disturbances, mild to severe skin lesions, kidney problems and encephalitis.

Since the transgenic rat has a similar phenotype to that of a transgenic mouse containing the pNL4-3 proviral DNA, the phenotype of the transgenic rat is most likely not due to an insertional inactivation event.

Example 3

Expression pattern of HIV in HIV transgenic rats

Expression of HIV genes in the HIV transgenic rats obtained as described in Example 1 was determined by RT-PCR as follows.

Rat tissues (i.e. eye, skin, muscle, brain, bone, heart, adrenal glands, kidney, large intestine, liver, lung, pancreas, small intestine, spleen, stomach, testicle, tongue, and thymus) were necropsied and snap-frozen in liquid nitrogen. The tissues were stored at −84° C. until processing. The tissues were homogenized in approximately 1 ml of Trizol (life Technologies) using a PowerGen Homogenizer (Fisher Scientific). After homogenation the samples were incubated at room temperature for 5 minutes to permit the complete dissociation of nucleoprotein complexes. 0.2 ml of chloroform was added to the samples before shaking for 2–3 minutes by hand. The milky pink samples were then centrifuged at 12,000 g for 15 minutes at 4° C. The mixture separated into a lower, red, phenol-chloroform phase, an interphase, and a colorless upper aqueous phase, which contains the RNA. The aqueous phase was transferred to a fresh tube, and mixed with 0.5 ml isopropyl alcohol. The samples were incubated for 10 minutes at room temperature then centrifuged at 12,000 g for 10 minutes at 4° C. The RNA precipitate formed a pellet on the side and bottom of the tube. The supernate was removed from the pellet. The pellet was then washed once with about 1 ml of 75% ethanol. The sample was then vortexed and centrifuged at 7,500 g for 5 minutes at 4° C. The supernate was once again removed, and the pellet was allowed to air-dry for up to 30 minutes. DEPC water was then added to redissolve the pellet. To assist in dissolving the pellet, the samples were incubated for 10 minutes (sometimes longer) at 60° C. The samples were then stored at −80° C.

cDNA was prepared from the RNA as follows. 20 μl of the RNA sample was incubated with 20 U of DNAse I (10 Units/μl) for 1 hour at 37° C. The sample was then phenol extracted (Trizol method above) to remove the DNA and DNAse protein from the RNA. The RNA was precipitated with ethanol and sodium acetate overnight. The pellet was washed, and dissolved as described above. 2 μl of the sample was diluted with 200 μl of deionized water. The sample was then quantitated to determine the amount of RNA present. 17 μl was made to contain 2 μg, of Dnased RNA. On ice, a cocktail of 1 1 Random Heximers 100 μM, 6 μl 5× Reverse Transcriptase Buffer, 3 μl DTT 0.1 M, 1.5 μl DNTP 10 mM, 0.5 μl RNAse inhibitor, and 1 μl Reverse Transcriptase (200 u) Moloney Murine Leukemia Virus Reverse Transcriptase was added to the Dnased RNA. For samples reversed transcribed with the Art7 primer, 1.6 μl Art7 and 5.4 μl 5× RT buffer was used. The mixture was incubated for 1 hour at 37° C. The samples were then heated at 95° C. for 5 minutes to kill the enzyme. The samples were immediately put on ice.

PCR was performed as follows. 5 μof cDNA was added to 40 μl of PCR SuperMix (Gibco). The PCR SuperMix contains 22 mM Tris-HCl (pH 8.4), 55 mM KCl, 1.65 mM MgCl$_2$, 220 μM dGTP, 220 μM dATP, 220 μM dTTP, 220 μM dCTP, 22 U recombinant Taq DNA Polymerase/ml, stabilizers. 5 μl of 5', 3' primers (20 μM) were added to the reaction mixture. The samples were first denatured for 3 minutes at 95° C. The parameters for PCR amplification were as follows: 35 cycles, each with denaturation at 95° C. for 1 minute, annealing at 60° C. for 2 minutes, and extension at 72° C. for 2 minutes. The final cycle was followed by a 5 minute extension at 72° C. The samples were then held a 4° C.

The sequences of the primers and probes used for cDNA synthesis and detection as well as the expected products are as described in Bruggeman et al. (1994) Virology 202:940. Since the mRNA encoding all HIV-1 proteins are processed from the same precursor RNA with alternative splicing and all HIV-1 mRNAs have identical 5' exons, the 5' sense primer used for all cDNA synthesis was US (TAG TAG CAT GCT CTC TCG ACG CAG GAC TCG GCT TGC; SEQ ID NO: 1). The primer pair US and ART7 (ATG ATC TGC AGT TCT ATT CCT TCG GGC CTG TCG; SEQ ID NO: 3) was used to amplify the tat, rev, and nef genes. Probing of the amplified products with S1 identifies a 402 bp tat fragment, while probing with S2 identifies 402 bp-tat and 219/225 bp-rev fragments and probing with S3 identifies 402 bp-tat, 219/225 bp-rev and 203 bp-nef fragments. The primer ART5 is downstream from the slice acceptor for vif and the primer ART2 is downstream from the initiation codon of Env. The primer pair ART5/US amplifies vif mRNA and generates a 338 bp fragment when probed with S4. Primers ART2 (ACC TCC TGC AGC ACA GGT ACC CCC ATA ATA GAC TGT G; SEQ ID NO: 2) and US was used to amplify env mRNA and generated a 446 and 665 bp product when probed with the S3 probe. The 5' and 3' primers for G3PDH and SK68 (5' AGC AGC AGG AAG CAC TAT GG; SEQ ID NO: 4) and SK69 (5' CCA GAC TGT GAG TTG CAA CAG; SEQ ID NO: 5) for Env were used to amplify regions of cDNA generated from random hexamers.

Following amplification, the reaction mixtures were subjected to electrophoresis, the nucleic acids were transferred onto a blot and the blot was hybridized with the following probes:

S1 GAG CCA GTA GAT CCT AGA CTA GAG C (SEQ ID NO: 6);
S2 CTT AGG CAT CTC CTA TGG CAG GAA (SEQ ID NO: 7);
S3 ACC TCG CAT GCG AAG AAG CGG AGA CAG CGA CGA AG (SEQ ID NO: 8); and
ENV TGA CGC TGA CGG TAC AGG CC (SEQ ID NO: 9).

The results of tissue expression analysis indicate the presence of transcripts of about 7 kb (full length gag-pol mRNA), 4 kb (singly spliced env. mRNA) and 2 kb (multiply spliced tat, rev, and nef mRNA) in numerous tissues including the eyes, skin, and muscle and moderate expression in the brain and heart, and light expression in bone and bladder. No detectable levels of Env mRNA were found in the adrenal glands, kidney, large intestine, liver, lung, pancreas, small intestine, spleen, stomach, testicle, tongue, and thymus.

Example 4 gp120 is present in the serum and on the surface of PBMCs in HIV transgenic rats Expression of the envelope protein in serum and PBMC was assayed by ELISA capture and flow cytometry, respectively. The ELISA assay indicated that two of the hemizygous transgenic animals containing gp120 in their sera at levels of approximately 145 pg/ml.

Multicolor flow cytometry of PBMCs was performed on a FACSCalibur (Becton-Dickinson Mountain View, Calif) as previously described (Taurog and El-Zaatari (1988) J Clin Invest 82, 987–92; Taurog et al. (1988) J Clin Invest 82, 987–92). Briefly, Ficoll-Hypaque purified peripheral blood mononuclear cells were incubated with saturating concentrations of F105 human anti-env antibody (available from the AIDS Repository), washed, then incubated with anti-human-FITC secondary antibody (available from Pharmigen Commercial). The staining was done in the presence of 1% human AB serum (available from Sigma Commercial). After washing, the cells were fixed in 1% paraformaldehyde before analysis on a FACScan flow cytometer (Becton Dickinson, Mountain View, Calif). Viable lymphocytes were selected for analysis by gating of forward and 90° light scatter.

Figure 2:
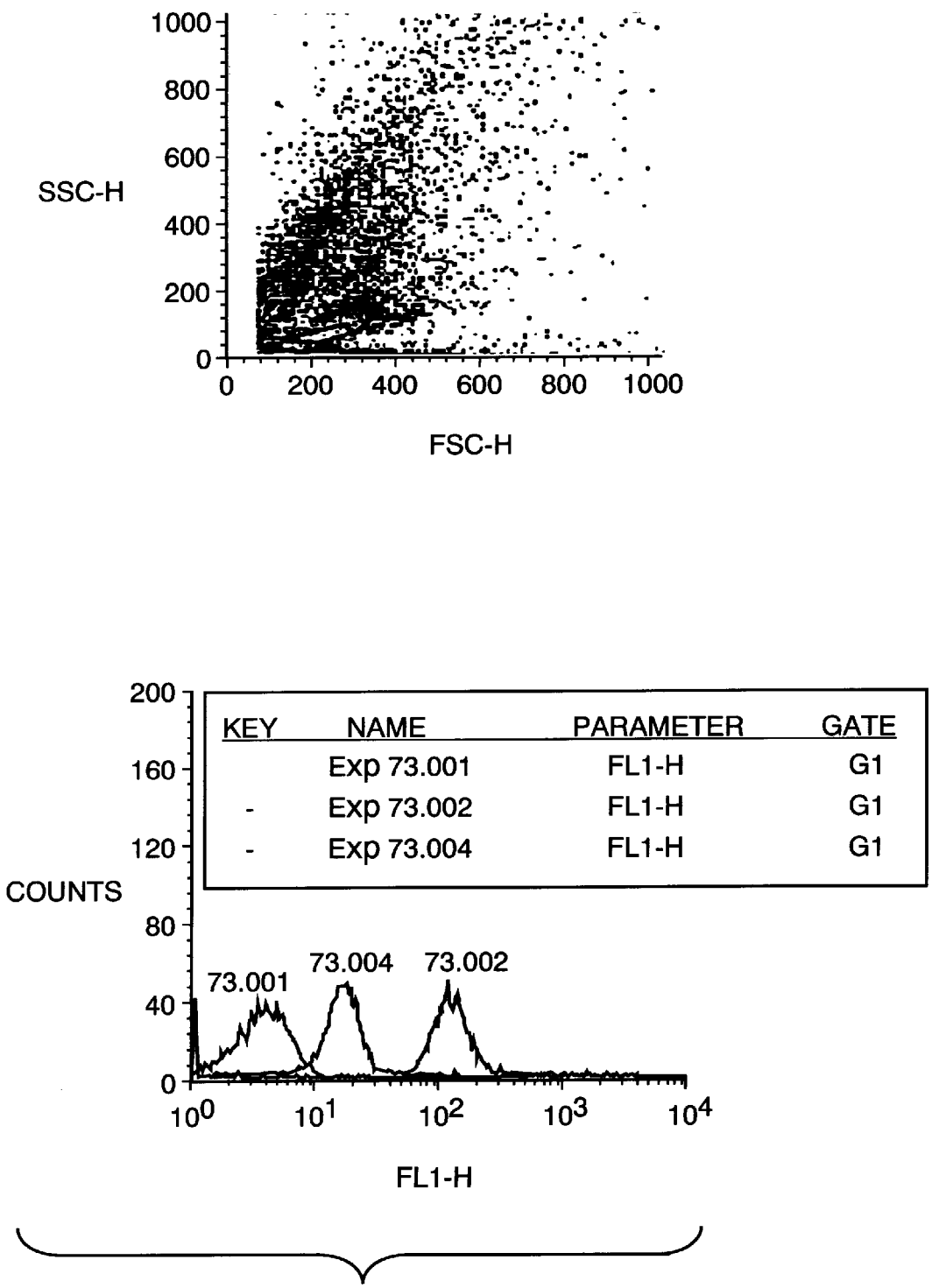
FIG. 2 shows the result of indirect immunofluorescence and flow cytometry analysis of peripheral blood mononuclear cells (PBMCs) of HIV-transgenic rats, indicating that the PBMCs express gp120 on their surface (73.001: no staining; 73.002: Surface staining for env with F105 human anti-env antibody plus anti-human-FITC secondary antibody; 73.004: Surface staining with anti-human-FITC secondary antibody alone).

The FACS analysis, which is shown in FIG. 2, indicates that gp120 was readily detectable on the surface of the entire PBMC population. Thus, the data indicate that, contrary to mice transgenic for pNL4-3:d1443, the gp120 env protein is expressed on the surface of PBMCs of IRV transgenic rats and shed into their serum.

Example 5

Production of an HIV/human CD4 double transgenic rat

A rat transgenic for HIV, e.g, HIV-1 and human CD4 can be prepared by crossing an HIV-1 transgenic rat described in the previous examples with a rat containing a human CD4 transgene and selecting for offspring carrying both transgenes.

A human CD4 transgenic rat can be prepared as follows. A construct containing human CD4 transgene, such as pES/CD4 (Louis Flamand; hCD4 is also described in Gillespie et al. (1993) Mol. Cell. Biol. 13:2952), containing a 6 kb Mlu 1-Sal 1 fragment (ES/CD4) with the CD4 structural gene and its regulatory sequence can be linearized and used to prepare transgenic rats using the technique of pronuclei injection described above for the preparation of the HIV transgenic rat.

The offspring is tested for the presence of the HIV transgene as described above and for the presence of the human CD4 transgene using the PCR primers that are specific for the human CD4 gene and which do not interact with the rat CD4 gene or by Southern blot hybridization using a probe hybridizing specifically to human and not to rat CD4. Expression of the transgene can be determined by Northern blot and/or flow cytometry or FACS analysis, as described above. For example, to detect hCD4 expression, PBMC can be resuspended at a concentration of $10^7$ cells per ml in cold PBS with 2% serum on ice. A total of $10^6$ cells can then be reacted with anti-human and anti-rat CD4 antibody conjugated with APC fluorochrome and subjected to analysis by flow cytometry. It has been observed previously that human and rat CD4 antibodies do not cross react.

Infection of hCD4 transgenic rats can be performed as follows. Mature (6 to 8 weeks old transgenic rats can be inoculated either intravenously (IV) or intraperitoneally (IP) with various concentrations of HIV (IIIB) (0.1–20 $TCID_{50}$) or with $10^5$ HIV-1 (IIIB)-infected CEM cells. Control animals can be non transgenic rats injected with non-infectious virus and hCD4 transgenic rats infected with the NSI HIV-1 (BA-L) or with diluted pellets from non-infected CEM cells. The presence of HIV-1 antibodies and viral antigen (p24) in the sera can then be analyzed every 2 weeks for the first two months and at 4 months post inoculation using a commercially available ELISA test. Rat PBMCs can be isolated on Ficoll-hypaque and $1.0 \times 10^6$ cells can be cultured with $0.3 \times 10^6$ CEM cells. Simultaneously, $10^6$ PBMC can be treated with 3 μg/ml of PHA overnight and then cultured with CEM. Cultures can be examined for CPE for 1 month and supernatant can be checked for antigen production by ELISA weekly.

Infection by HIV can also be tested in rats which are also trangenic for a construct containing the HIV-1 LTR upstream of DNA encoding the green fluorescent protein (GFP), for example. Infection of a cell containing this construct will result in stimulation of the LTR and therefore the GFP.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A transgenic rat, whose genome contains at least one copy of a human immunodeficiency virus type 1 (HIV-1) proviral DNA wherein the gag and pol genes are mutated to render the proviral DNA noninfectious, and wherein said rat develops at least one symptom of Acquired Immune Deficiency Syndrome (AIDS).

2. The transgenic rat of claim 1, wherein the HIV-1 proviral DNA has been introduced into said rat's genome via the vector pNL4-3:D1443.

3. The transgenic rat of claim 1, wherein HIV-1 gp120 protein is present on the surface of said rat's peripheral blood mononuclear cells (PBMCs).

4. The transgenic rat of claim 3, wherein the HIV-1 gp120 protein is also present in the rat's blood.

5. An isolated cell of the transgenic rat of claim 1.

6. The cell of claim 5 wherein the cell is a germ cell.

7. The cell of claim 5, wherein the cell is a somatic cell.

8. An isolated egg of the transgenic rat of claim 1.

9. An assay for indentifying a compound which reduces at least one symptom of AIDS in a subject, comprising the steps of:

(a) administering a test compound to an HIV-1 transgenic rat of claim 1; and (b) determining the severity of at least one symptom of AIDS in the transgenic rat of step (a), such that a reduction in the severity of said at least one symptom of AIDS in the transgenic rat to which the compound was administered relative to the severity of the said at least one symptom of AIDS in said transgenic rat before the compound was administered indicates that the compound reduces said at least one symptom of AIDS.

10. The assay of claim 9, wherein said at least one symptom of AIDS is selected from the group consisting of skin lesions, kidney lesions, cataract, and central nervous system (CNS) disturbances.

11. The assay of claim 9, wherein said at least one symptom of AIDS is the presence of HIV-1 gp120 on the PBMCs of the transgenic rat.

12. The assay of claim 9, wherein said at least one symptom of AIDS is the presence of HIV-1 gp120 in the blood of the transgenic rat.

13. A method of generating the transgenic rat of claim 1, comprising introducing into an embryo of a rat a HIV-1 proviral DNA (HIV-1) wherein the gag and pol genes are mutated to render the proviral DNA non-infectious, and permitting the embryo to develop into a rat containing said HIV-1 proviral DNA in its genome.

* * * * *

UNITED STATES PATENT AND TRADEMARK OFFICE
CERTIFICATE OF CORRECTION

PATENT NO. : 6,156,952
DATED : December 5, 2000
INVENTOR(S) : Joseph L. Bryant, William C. Reid, Harry G. Davis, Jr.

It is certified that error appears in the above-identified patent and that said Letters Patent is hereby corrected as shown below:

Title page,
Item "[73] Assignee :", delete "Constituent Institution of the University of Maryland System" and insert in place thereof -- University of Maryland Biotechnology Institute --.

Column 1,
Line 39, change "gp1 60" to -- gp160 --.

Column 2,
Line 31, change "lade" to -- clade --.

Column 4,
Line 43, change "thereof Alternatively" to -- thereof. Alternatively --.

Column 7,
Line 50, change "nef-p0460 1" to -- nef-p04601 --.

Column 9,
Line 14, change "M3843 1" to -- M38431 --.

Column 10,
Line 39, change "thereof A" to -- thereof. A --.

Column 11,
Line 14, change "Trans genic " to -- Transgenic --.
Line 46, change "pNL4-3:dI443" to -- pNL4-3:dl443 --.

UNITED STATES PATENT AND TRADEMARK OFFICE
CERTIFICATE OF CORRECTION

PATENT NO. : 6,156,952
DATED : December 5, 2000
INVENTOR(S) : Joseph L. Bryant, William C. Reid, Harry G. Davis, Jr.

It is certified that error appears in the above-identified patent and that said Letters Patent is hereby corrected as shown below:

Column 18,
Line 50, change "thereof Preferred" to -- thereof. Preferred --.

Column 21,
Line 2, delete "fir,"

Column 25,
Line 13, change "of 1 1" to -- of 1 µl of --.
Line 23, change "5µ of" -- 5µ of --.

Signed and Sealed this

Sixth Day of November, 2001

Attest:

NICHOLAS P. GODICI
*Attesting Officer*  *Acting Director of the United States Patent and Trademark Office*